United States Patent [19]

Brandt

[11] 4,366,577
[45] Dec. 28, 1982

[54] COMPUTED TOMOGRAPHY SYSTEM CABLE RETRACTOR

[75] Inventor: Richard T. Brandt, New Berlin, Wis.
[73] Assignee: General Electric Company, Schenectady, N.Y.
[21] Appl. No.: 282,897
[22] Filed: Jul. 13, 1981
[51] Int. Cl.³ .......................... H05G 1/02; A61B 6/00
[52] U.S. Cl. .......................................... 378/194; 378/4
[58] Field of Search .................................. 378/4, 194

[56] References Cited

U.S. PATENT DOCUMENTS

4,099,061  7/1978  Zink et al. ................................ 378/4
4,246,482  1/1981  Zupancic ............................ 378/194

Primary Examiner—Alfred E. Smith
Assistant Examiner—T. N. Grigsby
Attorney, Agent, or Firm—Ralph G. Hohenfeldt

[57] ABSTRACT

A cable retractor for a computed tomography scanner that is driven with a motor and a belt through two revolutions between clockwise and counterclockwise limits about a horizontal axis. An inner drum is fixed on the scanner for rotation therewith and a stationary outer drum is concentric to the inner drum. Cables are fastened where they enter the outer drum and exit the inner drum on their way to the scanner. A loop is formed in the cable in the circular channel defined by the concentric drums to provide enough cable length for the scanner to make two revolutions. A disk facing the channel is journalled for rotation on the inner drum. Pulleys extend axially from the disk to support the cable loop. The disk is belt driven so its angular motion is a constant fraction of the motion of the scanner whereby the pulleys move at the same rate as the loop to keep it supported as cable is reeled between the drums. Solenoid operated latching levers assure stopping the scanner rotation before the cables would be overstressed.

6 Claims, 12 Drawing Figures

FIG.12

COMPUTED TOMOGRAPHY SYSTEM CABLE RETRACTOR

BACKGROUND OF THE INVENTION

The invention disclosed herein pertains to computed X-ray tomography equipment. In particular, the invention comprises apparatus for controlling and protecting the cables that communicate between rotating and stationary parts such as between a gantry structure and the X-ray tube, X-ray detector and other components on the rotating X-ray scanner.

Typical computed tomography apparatus comprises a scanner base, basically a ring having a central opening, mounted for rotation about a generally horizontal axis on an upright member. The body being examined extends axially through the central opening and is supported on a cantilevered X-ray transmissive table top coincident with the axis of rotation. An X-ray source and its associated beam collimator are mounted on the scanner base on one side of the rotational axis and a multicell X-ray detector and its associated data acquisition device are mounted on the base on the other side of the axis. The X-ray beam is collimated into a thin fan-shaped configuration for scanning a thin layer of the body. The X-ray source is usually energized for about 360° of scanner rotation in either direction. The X-ray detector yields signals representative of X-ray attenuation along discrete bundles of rays in the beam. The signals are ultimately converted to digital data which is used by a computer to reconstruct an image of the cross-section or layer of the body that has been scanned as is well known.

A large number of electrical connections must be made between stationary parts of the tomography apparatus and the rotatable scanner base. For example, high voltage cables run to the anode and cathode of the rotating anode X-ray tube. A cable run to the anode rotating motor. Another cable supplies the servo motors that operate the X-ray beam collimator blades. Various cables run to position sensors. There are cables for conducting the multiplexed data from the X-ray detector and its data acquisition system to the computer.

It is desirable to avoid having the cables become tangled, or bent too sharply or overstressed in tension as they go around with the scanner base which may rotate nearly two full revolutions or 720° in each direction to execute a 360° scan of successive layers of the body. Cable tangling or disorderliness could result in the cables being effectively shortened in which case they might break when the power-driven scanner base approaches its rotational limits. Keeping the cables organized in a determinable way and free of undue stresses can be especially problematical where, as in the tomography apparatus to be described later, the scanner base makes about two revolutions for each body layer scanned. Even though the X-ray source is energized for only 360° or, by way of example, two seconds of rotation, the scanner base must rotate from a rest position through about 180° to allow acceleration up to a uniform speed before the X-ray beam is turned on for 360° of rotation. Then the scanner base must decelerate and come to a smooth stop so considerable angular overtravel must be permitted up to a limit. Excessive overtravel must also be avoided and measures must be taken to assure that the scanner base is positively stopped when the permissible rotational limit, that is determined by the length of the cables, is reached.

In some computed tomography equipment slip rings and brushes are used to provide electrically conductive paths between the rotating scanner electrical components and stationary components. This obviates some of the problems that arise with cables but it creates other problems such as the need for insulation for withstanding the high X-ray tube voltages, introduction of noise in the data channels and distortion and wear of the slip rings and their cooperating contacts.

SUMMARY OF THE INVENTION

Objects of the present invention are to provide a cable handling device or retractor that: reduces cable wear; minimizes load imposed by the cables on the scanner; reduces the power required to drive the cables and the scanner base; minimizes bending stresses in the cables; avoids developing any significant noise as a result of cable movement; and, keeps the cables arranged in an orderly and determinable fashion.

In accordance with the invention, the open-centered scanner base, which carries the X-ray source and detector, is journaled in an upright member for rotation about a nominally horizontal axis. A motor and belt drives the scanner base at the rotational speed desired for X-ray beam scanning. A cable supporting inner drum, on which the cable group assembly is reeled and unreeled, is mounted to the scanner base concentrically with the axis of rotation and, hence, the inner drum rotates at the speed of the scanner base. One end of the cable assembly is attached to the inner drum. An outer drum or shroud that remains stationary is fixed to the upright member concentrically with the inner drum. Another end of the cable is fastened to the outer drum. The outside periphery of the rotatable inner drum and the inside of the stationary outer shroud define a circular channel. The action of unreeling and reeling the cable assembly by rotation of the inner drum causes a loop of cable to be formed in the channel.

An open-centered disk is disposed over the channel. The disk is mounted for rotation on the inner drum. The disk is driven with the same motor that drives the base and inner drum but at an angular rate or rotational speed which is a fixed fraction of the rotational speed of the inner drum. The disk carries several circumferentially spaced apart stud shafts that project into the channel along its center. The shafts each have a cable supporting pulley rotatable on them. The pulleys have diameters roughly equal to the radial width of the channel minus the thickness of two cable runs. As indicated, the loop of the cable has an angular motion with respect to the inner drum which is a fraction of the inner drum rotational speed. Thus, the disk and, hence, the pulleys are orbited around the channel at an appropriate speed for one pulley to fit into the loop or reentrant bend in the cable for transferring cable from the inner drum to the outer stationary shroud or drum while portions of the cable extending away from the bend of the loop are supported on the other pulleys.

The manner in which the objects mentioned above and other objects of the invention are achieved will be evident in the more detailed description of a preferred embodiment of the invention which will now be set forth in reference to the drawings.

DESCRIPTION OF A PREFERRED EMBODIMENT

Figure 1:
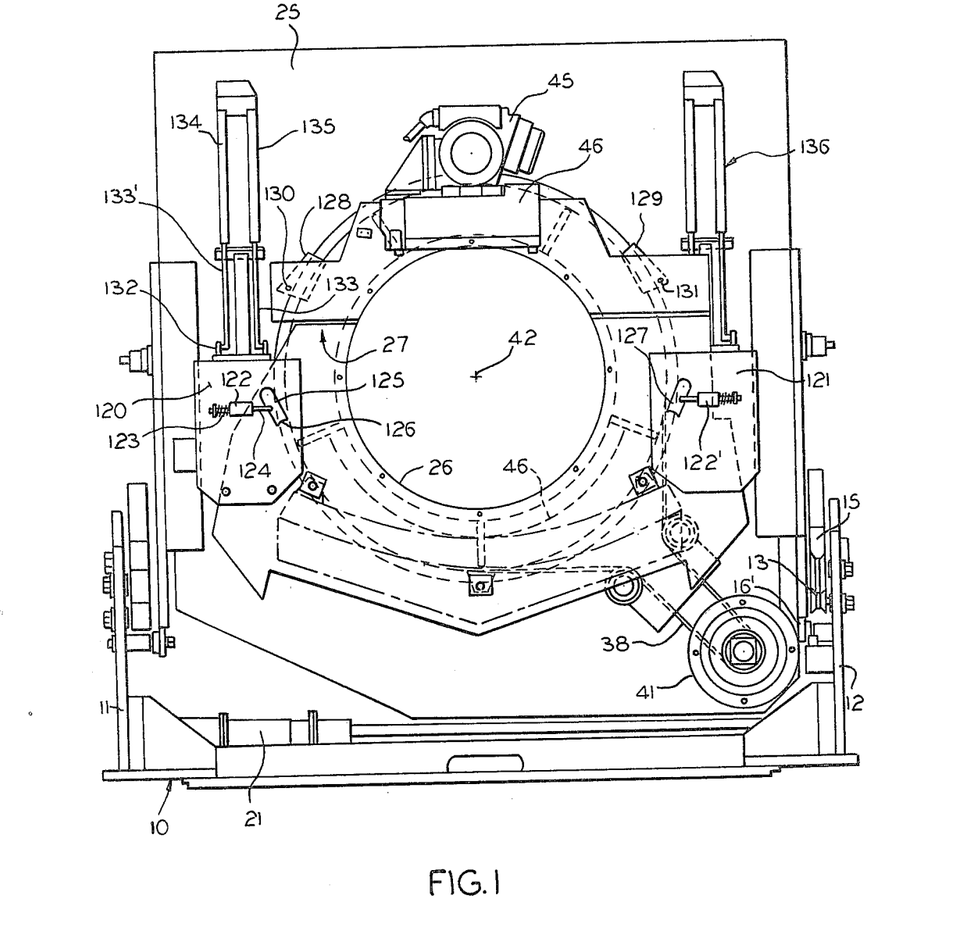
FIG. 1 is a front elevation view of computed tomography scanning apparatus which incorporates the new cable retractor, the decorative shrouds of said apparatus being omitted to permit depicting the operative apparatus more clearly.
Figure 2:
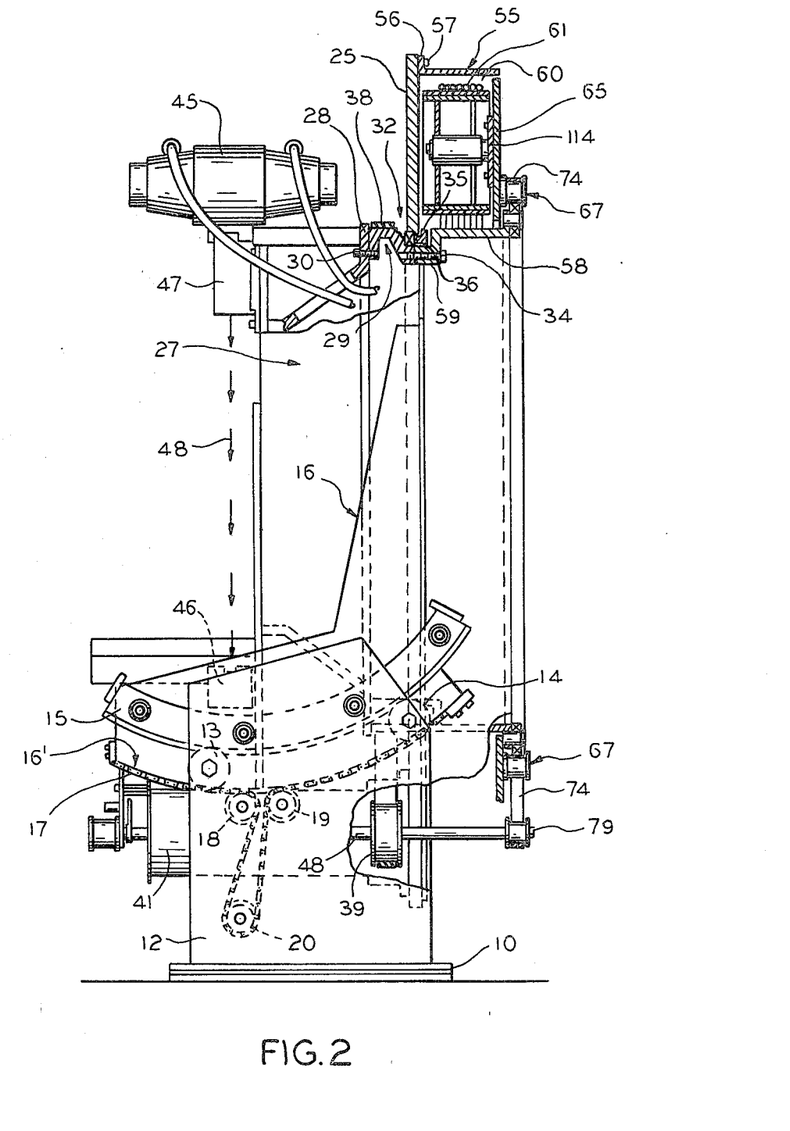
FIG. 2 is a right side elevation, partially in section, of the apparatus shown in FIG. 1, the position of the rectractor in FIG. 2 corresponding to the counterclockwise limit of rotation of the scanner when viewed from the front as in FIG. 1 whereas the FIG. 7 diagram shows the retractor from the rear of the scanner when the scanner is at its counterclockwise limit.

Referring to FIGS. 1 and 2, the X-ray scanner apparatus comprises a base 10 that is anchored to the floor and two upstanding laterally spaced apart plate members 11 and 12. Typical plate member 12 has V-shaped rollers mounted to it such as those marked 13 and 14. As shown best in FIG. 2, a rocker segment 15 rests on the rollers for rocking thereon. Rocker segment 15 has a V-shaped lower edge that complements the grooves in rollers 13 and 14. Typical rocker 15 is fastened to one of two laterally spaced apart upright members 16. The visible one in FIG. 2 has a curved lower portion 16' that is concentric to the curve of the rocker 15. The rocker is driven by a chain 17 that is fastened at both of its ends to curved portion 16' and loops around a driving sprocket 20. Sprocket 20 is driven by a reversible motor 21 which appears in FIG. 1. Thus, the upright members can be tilted from the vertical position in which they are shown.

Figure 10:
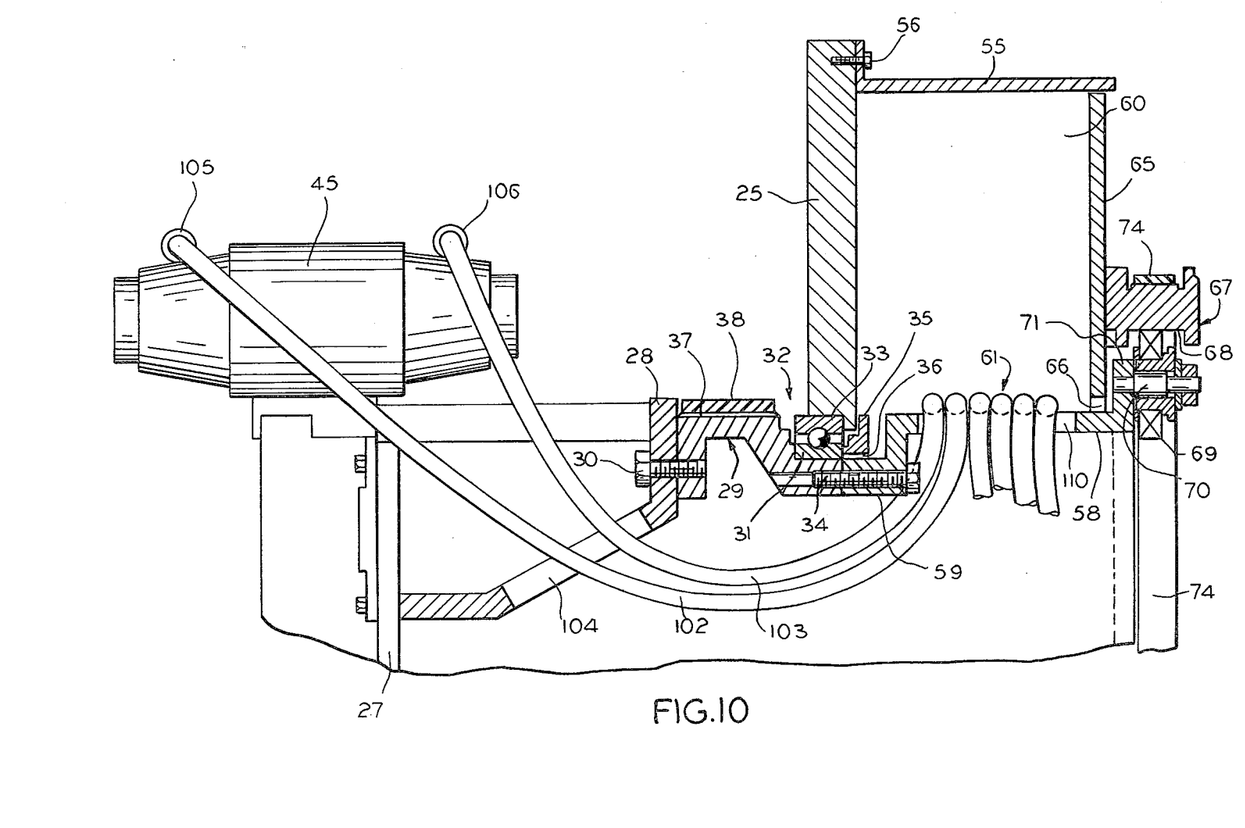
FIG. 10 is an enlargement of the upper portion of FIG. 2 but with the cable retractor rotated to a position midway between its clockwise and counterclockwise limits to correspond with the FIG. 8 diagram.

A nominally vertical plate 25 is mounted to laterally spaced apart upright members 16. This plate has a large central opening concentric to the large central opening 26, see FIG. 1, in a generally cone-shaped scanner base 27. As can be seen in FIGS. 2 and 10, scanner base 27 has a radially extending annular rim 28. An annular member 29 which serves as a pulley is fastened to scanner base rim 28 at circumferentially spaced apart locations by cap screws such as the one marked 30. Pulley 29 has the inner race 31 or a ball bearing 32 pressed on it. As can be seen best in FIG. 10, the outer race 33 of bearing 32 is fitted into nonrotating vertical plate 25.

The bearing is retained with a retaining ring 35 that has some circumferentially spaced apart cutaways such as the one marked 36 in FIG. 10. Machine screws, now shown, pass through ring 35 between cutaways and screw into pulley 29 to secure retainer ring 35 against the inner race of the bearing. It will be evident from the description thus far that scanner base 27 is journaled for rotation about a nominally horizontal axis relative to nonrotating vertical plate 25 which is supported on the uprights. This axis is marked 42 in FIG. 1. When plate 25 is tilted from vertical on its rockers, axis 42 will be inclined to horizontal so the X-ray beam can pass through the body at an angle with respect to vertical to the option of the radiologist.

The annular or ring-type pulley 29 has axially extending teeth 37 on its outer periphery. The toothed pulley has a toothed belt 38 running on it. As shown in FIGS. 1 and 2, belt 38 is driven by a toothed pulley 39 that is fastened to the shaft 40 of a reversible electric motor 41. When the motor is energized, it drives the scanner base 27 rotationally by means of belt 38.

As shown in FIGS 1, 2 and 10, an X-ray tube casing 45 is mounted on scanner base 27 on one side of nominally horizontal axis 43. A multiple cell X-ray detector 46 is mounted to scanner base 27 on the other side of horizontal axis 43. The X-ray beam emerging from X-ray tube casing 45 passes through a beam collimator 47 which results in the beam emerging from the collimator being thin in the axial direction and having a fan-shape in a plane to which axis 43 is perpendicular. The path of the thin beam is indicated by the arrows 48 in FIG. 2. As is well known, the body which is to be scanned with the X-ray beam is supported colinear with axis 43. During a rotational scan, X-ray detector 46 produces electric signals indicative of X-ray attenuation of the ray bundles after they have emerged from the body and, as is well known, these signals are variously processed and ultimately used by a computer to reconstruct an image of a layer of the body through which the thin X-ray beam passes.

Valid X-ray attenuation data is obtained during the time that the X-ray tube 45 is energized and making a 360° orbit jointly with the detector 46 around the body. However, the X-ray tube and, hence, the scanner base must be oribiting or rotating at a constant angular rate during 360° of rotation during which the X-ray tube is energized. Thus, in the illustrative embodiment, the first 180 degrees of rotation are used for accelerating the scanner base up to constant speed. During the next 360° of rotation at a constant speed the X-ray tube is energized and attenuation data is collected. At the end of the scan, another 180° is allowed for decelerating and stopping rotation of the scanner base 27. Thus, it will be evident that for every body layer that is scanned the scanner base will make two revolutions in one direction. Usually, after a scan in one direction is made, the body being examined is indexed longitudinally by an amount equal to the thickness of the X-ray beam and another scan is made in the opposite direction and another two revolutions of the scanner base occur. It will be evident then that the cables which communicate between the stationary parts of the scanner apparatus and rotating parts such as the X-ray tube and the X-ray detector must be long enough to allow for two revolutions of the scanner base.

Figure 3:
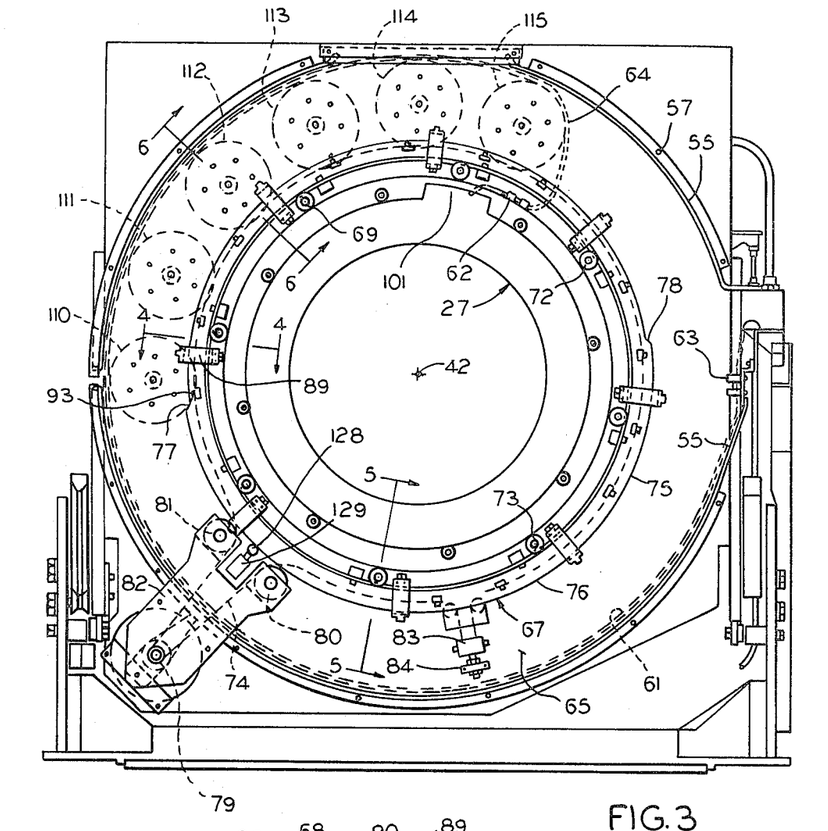
FIG. 3 is a rear elevation view of the scanning apparatus in FIG. 1 looking directly at the cable retractor.

The new cable handling and control device will now be discussed. For convenience, the device will be called a cable retractor. Referring to FIGS. 2 and 3, the retractor in the illustrative embodiment is located rearwardly of scanner base 27 and nominally vertical plate 25. As can be seen particularly well in FIG. 2, the retractor comprises an outer nonrotatable drum or axially extending cylinder 55 which is provided with a flange 56 for facilitating fastening it to vertical plate 25 by means of angularly spaced apart mechine screws such as the one marked 57. As shown in FIGS. 2, 3, 5 and 10, an inner drum 58 is provided with a plurality of angularly apaced apart pads 59 through which cap screws 34 pass to fasten inner drum 58 to the driven scanner base pulley 29 which turns with scanner base 27. The pads 59 pass through the cutaways 36 in bearing retainer ring 35. It will be evident that when scanner base 27 is rotated under the influence of driving belt 38, inner drum 58 will rotate with the scanner base. The concentrically arranged outer stationary drum 55 and inner rotatable drum 58 define an axially extending channel 60. The group of electric cables, which is generally designated by the reference numeral 61, resides in channel 60.

Figure 7:
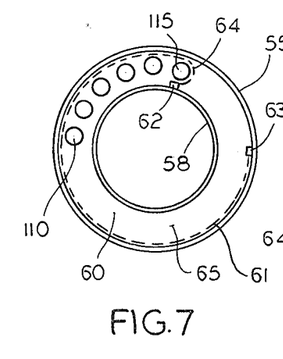
FIGS. 7, 8 and 9 are diagrams of the cable retractor in different operational stages.
Figure 8:
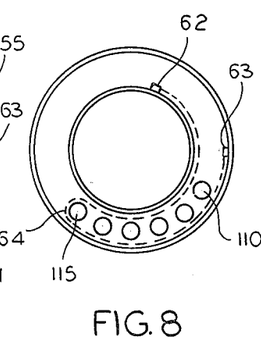
Figure 9:
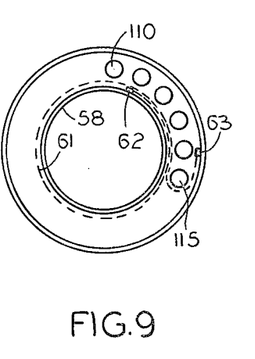

As shown in the FIG. 7–9 diagrams, one end of the cable group is fastened at a point marked 62 to inner rotatable drum 58 and the other end of the cable group is fastened at 63 near an inlet to outer stationary drum 55. One may see in the diagrams that the cable reels and unreels from the inner drum and is correspondingly picked up from and laid down on the outer drum. The cable forms a loop in channel 60 which is defined between concentric rotating drum 58 and fixed outer drum 55. The loop is identified by the numeral 64. During rotation of the scanner base 27, the cable loop moves circularly in the channel 60. The angular motion of the loop is less than the angular motion of the scanner base and, hence, is less than the angular motion of the inner drum 58.

Means are provided for maintaining control over the cable bundle 61 and its loop within channel 60. Objectives are to keep the heavy cables in the group organized in a predetermined fashion and to minimize the noise that might result from the cable bundle slapping against the outer drum as the cable is unreeled from the inner drum.

As can be seen particularly well in FIGS. 2, 3 and 10, in accordance with the invention, channel 60 is closed at its end with a disk 65. The disk has a central opening 66 for permitting it to be disposed circumjacent inner drum 58 with the axis of the disk coincident with the horizontal rotational axis 42 of the scanner base. A large ring-type pulley 67 is fastened concentrically to disk 65. Pulley 67 is journaled for rotation on inner drum 58 so the pulley 67 can rotate at a different angular rate than that of the inner drum and scanner base. As can be seen particularly well in FIGS. 5 and 10, pulley 67 has a smooth internal periphery 68 that runs on a plurality of rollers 69 which are journaled on stud shafts 70 that are, in turn, anchored in angularly spaced apart radially extending pads 71 which are integral with inner drum 58. A typical roller 69 and several others marked 72, 73 are also shown in FIG. 3. The outer periphery of pulley 67 is smooth but is engaged to be driven by a toothed belt 74. The belt 74 wraps around opposite sides of pulley 67 to a place where the ends of the belt are gripped by a clamp 83 that is coupled to an adjustable belt tightened 84 which is fastened to disk 65. FIG. 3 shows how the disk driving belt loops around driving pulley 79 and diverges in opposite directions around idler pulleys 81 and 82 which are mounted on a bracket 82. The radially extending rim 75 of pulley 67 is actually a cam whose purpose will be described later. As can be seen in FIG. 3, the radius of rim 75 is reduced over a region marked 76 to thereby create two approximately 180° spaced apart cam risers 77 and 78. FIG. 2 shows how belt 74, which drives pulley 67 and, hence, disk 65 rotationally, runs around a small peripherally toothed driving pulley 79 which is fastened to the shaft 40 that extends out of motor 41. It will be evident that when motor 41 turns the scanner base by means of belt driving pulley 39, the other pulley 79 on the same motor shaft will drive disk 65. Disk 65 is driven so that its angular motion is a constant fraction of the angular motion of the scanner base and, hence, of inner drum 58. The manner in which the ratio between the angular motions of disk 65 and inner drum 58 are determined will be discussed in detail later.

Figure 4:
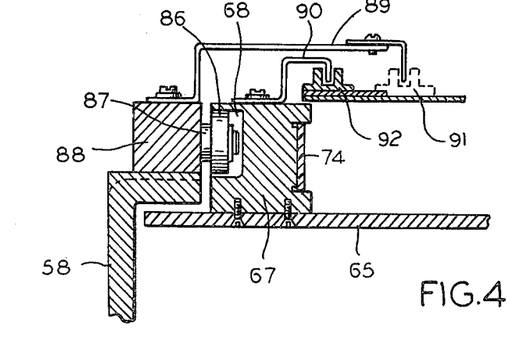
FIG. 4 is a partial section taken on a line corresponding to 4—4 in FIG. 3.
Figure 5:
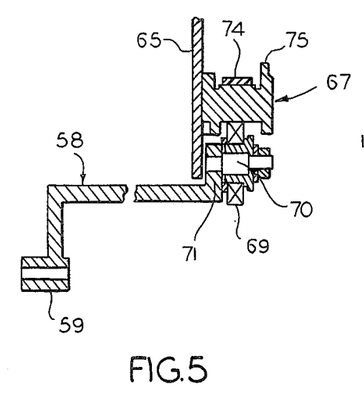
FIG. 5 is a partial section taken on a line corresponding to 5—5 in FIG. 3.

As shown in FIG. 4, ring pulley 67 which carries disk 65 is retained against shifting axially by means of another set of rollers such as the one marked 86 in FIG. 4. Rollers 86 turn on stud shafts 87 that are anchored on blocks 88 which are in turn fastened to inner drum 58. As shown in FIG. 4, shutter elements 89 and 80 are carried on block 88 and pulley 67, respectively. These shutter elements alternately block and unblock light beams in photosensitive devices 91 and 92 which provide electric signal information indicative of the angular position of some of the relatively movable parts which signals are used for purposes that do not have to be described to understand how the new cable retractor is constructed and functions. Axial motion constraining roller 86 is concealed under shutter bar 89 in FIG. 3. As can be seen by inspection of FIG. 3, there are eight rollers equivalent to roller 86 under shutter bars in FIG. 3 and they are equiangularly spaced. There are also additional rollers comparable to roller 86 and one of them is marked 93 in FIG. 3.

Figures 11, 12:
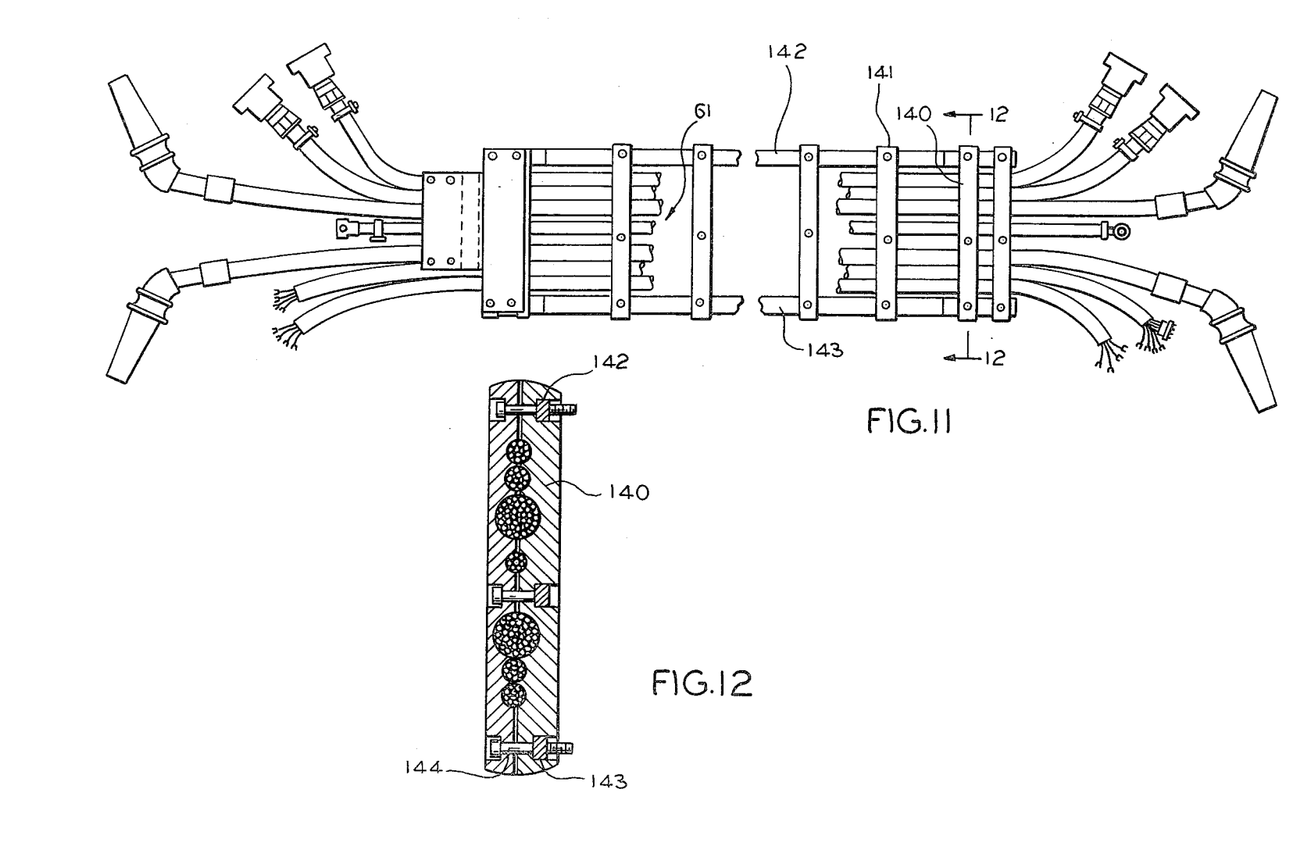
FIG. 11 is a plan view of a typical cable group that might be handled and controlled by the retractor.
FIG. 12 is a section taken on a line corresponding with 12—12 in FIG. 11.

The cable group 61 which is shown in detail in FIG. 11 is shown in dashed lines in FIG. 3. The cables are disposed in annular channel 60 which is defined by concentric outer stationary drum 55 and inner rotating drum 58. The cables are fastened at one end to outer drum 55 with a clamp 63 and to inner drum 58 with a clamp 62 as was previously mentioned in connection with the diagrams in FIGS. 7–9. Referring to FIG. 3, for that particular rotational position of the scanner base 27, the cables 61 are shown to lay along the inner surface of outer drum 55 and make a substantially semicircular loop in a portion of the cable marked 64. This same reference numeral 64 is used to indicate the loop for other rotational positions of the scanner and inner drum relative to the outer drum as, for instance, in FIGS. 7–9. In FIG. 3, one may see that since the cable group 61 is clamped at its inner end to the inner drum 58 with clamp 62 it is effectively clamped to scanner base 27. As shown in FIG. 10, where the retractor is in a rotational position that differs from its position in FIG. 3, the cables run through an opening 101 with an inner drum 58 to connect with various electrical components on scanner base 27. To illustrate, two of the cables marked 102 and 103 in FIG. 10, run through an opening 104 in the scanner base to connectors 105 and 106 on the X-ray tube casing 45. Note that in FIG. 10, the retractor is rotated to the midway or rotational position it has in the FIG. 8 diagram so none of the pulleys 110–115 (to be described later) appear in channel 60 in FIG. 10.

The cable group 61, when reeled on inner drum 58 has an effective radius of $r_i$. The cable when constrained to lie along the inside of the outer drum 55, has an effective radius of $r_o$. The action of unreeling the cable by rotation of the inner drum (which is fastened to the scanning base 27 and rotates with it) causes the loop of cable 64 to be formed. The radius of this loop is equal to $(r_o - r_i)/2$. This loop of cable has an angular motion ($\theta$) with respect to the inner drum 58 of:

$$\theta_{loop} = \frac{r_i}{r_i + r_o} (\theta_{inner\ drum}) \qquad (\text{Eq. 1})$$

Figure 6:
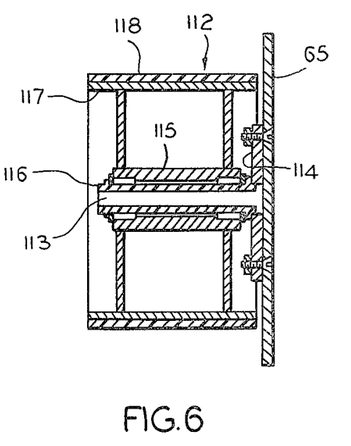
FIG. 6 is a section taken through one of the cable supporting pulleys on a line corresponding with 6—6 in FIG. 3 with parts other than the pulley and the disk on which it is mounted being omitted for the sake of clarity.

Referring to the FIGS. 7-9 diagrams, one may see that in the ideal case where gravity would not be a factor, action of the cable would be to unreel from the inner drum 58 and reel onto the inside of outer drum 55. Because the cables operate in a vertical plane, several pulleys are used to maintain the cable loop progression defined in Equation 1 when the cable is acted upon by the force of gravity and also by the inner drum or scanning base acceleration forces. The pulleys just referred to are shown as dashed line circles in FIG. 3 where they are given the reference numerals 110-115. In the illustrative embodiment there are six such pulleys. A typical pulley 112 is shown in the FIG. 6 sectional view. It is journaled for rotation on a stud shaft 113 which is welded into a base plate 114. The base plates 114 are anchored to disk 65 which is juxtaposed to the channel defined by the concentrically related outer and inner drums. The typical pulley comprises a hub 115 in which there is a bushing 116 made of a material such as nylon which requires no lubrication. The typical pulley comprises a metal cylindrical shell 117 that is covered with a layer of pliable cushioning material 118 to suppress noise and reduce cable wear.

The terms clockwise and counterclockwise as used herein refer to rotational directions of scanner base 27 as viewed from the front of the apparatus as it is viewed in FIG. 1.

FIG. 7 shows the disposition of the cable group 61 when the inner drum 58 (and the scanner base 27 to which it is fastened) is rotated to its counterclockwise limit after having made two revolutions in the counterclockwise direction. In accordance with Equation 1, cable loop 64 travels at a fraction of the angular motion of the inner drum. That fraction is represented by $r_i/r_i + r_o$. Referring to FIG. 2, the ratio of the diameter of the driven pulley 29 on scanner base 27 to the driving pulley 39 on the motor shaft is chosen so that fixed speed reversible motor 41 will drive the scanner base rotationally at a speed that is appropriate for gathering the X-ray attenuation data. Typically, as in the illustrated embodiment, a 360° scan of the body is made in two seconds. A little more time is added for acceleration and deceleration of the scanner base. The ratio of the diameter of ring-like pulley 67 on disk 65 to the diameter of its driving pulley 79 on the motor shaft 41 is substantially greater than the previously mentioned ratio in which case the angular motion of disk 65 will be a fraction of the angular motion of the scanner base. In fact, the disk 65 is rotated at a rate which results in the leading pulley 115 carried thereon remaining coincident with the loop 64 that is formed in the cable. In other words, all of the pulleys 110-115 move in a circle at the angular rate at which the cable loop would move by itself. By way of example and not limitation, in a commercial embodiment, the ratio of the diameter of scanner base pulley 29 to its driving pulley 39 is 12:1 to use a numerical example. The ratio of the diameter of pulley 67 on disk 65 to its driving pulley 79 is 30:1. It will be evident that in this example annular disk 65 will move four-tenths of the angular movement of scanner base 27 and the cable supporting pulleys would orbit at a corresponding angular rate. Thus, using the numerical example, for 720° of inner drum rotation the pulley 67 and its cam and disk 65 rotate four-tenths as much or 288°. For 360° of inner drum rotation the disk would rotate 144°.

When the scanner base and inner drum 58 begin to rotate in the clockwise direction from the counterclockwise limit depicted in FIG. 7, the cable group portion leading back from clamp 62 on the inner drum begins to reel onto the outer periphery of the inner drum 58 and off of the inner periphery of outer drum 55. FIG. 8 shows the disposition of cable group 61 when one full 360° rotation of the scanner base and inner drum 62 has been completed. In FIG. 9, the scanner base and drum 62 have reached their clockwise rotational limit where they have rotated about 720° or two revolutions from the position in which they are depicted in FIG. 7. In FIG. 9, one may see that a substantial portion of the cable 61 is now reeled on inner drum 58. For any angular position of the inner drum, pulley 115 on disk 65 is always kept within the cable loop 64. The other pulleys 110-114 always support the cable against falling off of inner drum 58 and onto the outer drum 55 or from the outer drum 55 onto the inner drum 58, depending on the rotational position of the inner drum and the scanner base to which it is attached.

Means are provided for assuring that the scanner base will not rotate beyond predetermined limits at which a tensile stress might be imposed on the cables. Means are also provided for assuring that the scanner base rotation will be positively stopped before the cables are subjected to tensile stress. These means will now be discussed.

Refer again to FIG. 1 which is a view of the front of the scanner base 27. Adjacent this base and substantially diametrically opposite of each other are a pair of plates 120 and 121 which are mounted for yielding slightly upwardly. Typical plate 120 has a solenoid coil 122 mounted to it. The magnetic plunger within the solenoid is biased to the right by means of a coil spring 123. A solenoid plunger 124 is pivotally connected to a pivotally mounted and swingable latch lever 125 that has a recessed end 126. The solenoid assembly on the other plate 121 is similar to that just described. It comprises a solenoid 122′ and latching lever 127.

As shown in FIG. 1, there are an angularly spaced-apart pair of brackets 128 and 129 fastened to scanner base 27. The brackets have pins 130 and 131, respectively, extending from them in the axial direction. By means which will be explained, solenoids 122 and 122′ are maintained in a deenergized state during the first 120° of rotation of the scanner base from either its counterclockwise or clockwise limit. When the solenoids are energized, both latch levers 127 and 125 will be retracted out of the orbital path of pins 130 and 131. Assume for the sake of example that in FIG. 1 scanner base 27 is rotating clockwise so that typical stop pin 130 orbits clockwise. During the X-ray scanning revolution it will clear past both latching levers 127 and 125 since the solenoids are energized. As a result of a cam operating a switch, as will be described, sometime before the scanner base reaches its rotational limit in one direction, that is, before the base has completed its second revolution, solenoids 122 and 122′ become deenergized so that the latch levers 125 and 127 are disposed in the orbital path of stop pins 130 and 131. For the sake of illustration, assume that the scanner base and the inner drum 58 thereon is to rotate clockwise as viewed from the front of the machine in FIG. 1 and counterclockwise as viewed from the rear of the machine and looking at the cable retractor as in FIG. 8. Referring to FIG. 1, stop pin 130 would now be orbiting clockwise and would pass latching lever 127 in the course of the scanner base making its second revolution. After passing latching lever 127, the solenoids become deenergized and, under the influence of biasing spring 123, the latching levers go into the orbital paths of the stop pins. This would occur when stop pin 130 is moving between latching lever 127 toward latching lever 125. With latching lever 125 in the path of pin 130, the pin would strike the recess 26 in the end of latching lever 125 for the latching lever to perform its scanner base stopping function. For rotation of the scanner base in the opposite direction in FIG. 1, latching lever 127 would perform the stopping function.

Typical solenoid supporting plate 120 is coupled by means of a bracket 132 to plunger rods 133 and 133' which extend out of cylinders 134 and 135. The cylinders and rods comprise what is known as a gas spring. A gas spring has the properties of bringing about constant deceleration of a moving object. The Gas Spring Corporation is one source of such devices. Gas springs are analagous to counterbalancing systems which maintain a constant force regardless of their position. As used in the apparatus being described, typical plunger rods 133 and 133' yield and impose a constant resisting force on the plate 120 which carries the solenoid operated latching lever 125, for example. Smooth stopping of scanner base rotation results. Stopping motion in the counterclockwise direction is achieved with a similar constant force-applying device which is generally designated by the reference numeral 136.

The means for controlling energization and deenergization of latching lever solenoids 122 and 122' comprise the previously mentioned cam 75 which forms part of the ring-type pulley 75 that drives disk 65. As shown in FIG. 3, the cam has two risers 77 and 78. A switch 129 is disposed adjacent the orbital path of the cam risers and in this particular embodiment, switch 129 is located between idler pulleys 80 and 81 over which the belt that drives the disk supporting pulley 67 runs. Switch 129 has a rockable operating lever on whose end there is a roller 128. When the roller goes on or off of the cam risers, the lever is pivoted and the switch is actuated. Whenever the switch is actuated, it closes a circuit, not shown, in which solenoids 122 and 122' are connected so that the solenoids are energized. As explained earlier, pulley 67 which carries disk 65 moves through an angle that is a fraction of the angle through which the scanner base 27 for driving pulley 29 moves when motor 41 drives both pulleys together. Thus the rear disk-carrying pulley 67 rotates less than one revolution when the front scanner 27 rotating pulley 29 rotates a full revolution. Thus, the cam risers do not reach the operating lever 128 of switch 129 for the first 120° of rotation of the front pulley 29 and, hence, scanner base 27. Using the numerical example which was used for illustrative purposes and not limitation earlier, scanner base 27 along with its driving pulley 29 rotates through a total angle of 720°. While executing this amount of angular motion, the rear disk-carrying pulley 67 would have four-tenths as much motion or a total of 288°. After the first 120° of rotation of the scanner base from either limit, the rear pulley 67 would turn only 48° so that the cam risers would just reach the switch lever. When the cam risers reach the lever 128 of switch 129 the switch is transferred to its closed circuit state and the solenoids become energized. This retracts the latching levers 125 and 127 from the orbital path of the stop pins 130 and 131 to allow 48° of scanner base rotational motion as previously described.

The cable group 61 is shown in detail in FIGS. 11 and 12. Various cables are clamped and held in substantially the same plane by clamps such as the ones marked 140 and 141 in FIG. 11. The clamps are spanned by a pair of spring steel members or bands 142 and 143 which are held in place by bolts such as the one marked 144 which hold the two halves of the clamps together. Spring steel bands 142 and 143 provide a spring force which tends to force the cable group into good contact with the inner and outer drums of the cable retractor.

Although a preferred embodiment of the new invention has been described in substantial detail, such description is intended to be illustrative rather than limiting, for the invention may be variously embodied and is to be limited only by interpretation of the claims which follow.

I claim:

1. X-ray apparatus having improved means for guiding cables running between stationary parts and electrical devices on rotating parts, comprising:
   support means,
   a base having an opening and being mounted on the support means for rotation about a nominally horizontal axis extending through the opening,
   said electrical devices including X-ray source means mounted to the base on one side of said axis and X-ray detector means mounted to the base on the other side of said axis for jointly rotating about a space for being occupied by an X-ray examination subject,
   inner axially extending drum means fastened to said base for rotation therewith and having a radially outwardly presented peripheral surface concentric to and radially spaced from said axis, said drum means having an opening for cables to pass through,
   outer axially extending fixedly mounted drum means having a radially inwardly presented peripheral surface radially spaced from and concentric to said surface on said inner drum means to define a circular channel therewith, said second drum means having an opening for cables to pass through,
   a group of cables and means fastening said group near said opening in the fixedly mounted outer drum means and near said opening in the rotatable inner drum means, said cables in the group having sufficient length to form a loop that moves angularly in said channel when said inner drum is being rotated,
   disk means presented toward said channel and means mounting said disk means for rotation independently of said inner drum means,
   a plurality of pulleys mounted to said disk means for rotation about parallel axes extending into said channel, the pulleys being angularly spaced and one of the pulleys being disposed in said cable loop and other of the pulleys being disposed between portions of the cable extending away from the loop,
   means for driving said base and said inner drum thereon rotationally and means for simultaneously driving said disk means rotationally for the angular motion of the disk to be the required fraction of the angular motion of the inner drum that results in said pulleys having an angular motion corresponding to the angular motion of the loop in the cables.

2. The apparatus according to claim 1 wherein said means for driving the base and the inner drum rotationally and for simultaneously driving the disk means rotationally comprises:
- a reversible electric motor having a shaft and first and second belt driving pulleys fastened to the shaft,
- a first driven pulley mounted to said base concentrically to said horizontal axis and a belt coupling said first driving pulley to said first driven pulley, the driven pulley having a diameter substantially greater than the driving pulley,
- a second driven pulley mounted to said disk means concentrically to said horizontal axis and a belt coupling said second driving pulley to said second driven pulley, the second driven pulley having a diameter substantially greater than the second driving pulley,
- the ratios of the pulleys being such that said angular motion of the disk means is said constant fraction of the angular motion of the inner drum.

3. The apparatus according to claim 1 wherein $R_i$ represents the radius of the inner drum relative to said horizontal axis, $R_o$ represents the radius of the outer drum, $(R_o-R_i)/2$ represents the radius from said horizontal axis to the center of said cable loop, $\theta_{loop}$ represents the angular motion of the cable loop and also the required angular motion of the disk means to keep the pulleys on the disk means in conformance with the cable loop and, $\theta_{inner\ drum}$ represents the angular motion of the inner drum and the angular motion $\theta_{loop}$ at which the disk means must be driven relative to the angular motion $\theta_{inner\ drum}$ at which the inner drum must be driven is defined as $$\frac{\theta_{loop}}{\theta_{inner\ drum}} = \frac{R_i}{R_i + R_o}.$$

4. The apparatus according to claim 1 including bearing means for supporting said disk means for rotation on the inner drum.

5. The apparatus according to any one of claims 1, 2, 3 or 4 including:
- a pair of angularly spaced apart abutment elements mounted to said base for orbiting with the base in a predetermined path,
- a pair of movable stop elements angularly spaced apart and radially spaced from said horizontal axis, said stop elements being disposed adjacent the rotatable base, one of the stop elements being for selectively stopping rotation of the base in one direction and the other for stopping rotation in the opposite direction,
- electroresponsive means operatively coupled to said stop elements, respectively, said means causing said stop elements to be retracted from the orbital path of the stop elements when the means are energized, and means for advancing said stop elements into the path when the electroresponsive means are deenergized,
- switch means for controlling energization and deenergization of said electroresponsive means, said switch means including a switch operator and being operative to energize said electroresponsive means for keeping said stop elements retracted during the time that said base is making a revolution centered between the rotational limits toward the other,
- cam means mounted for rotation with said disk in the path of said switch operator, said disk making only part of a revolution while said base makes said centered revolution such that the cam means reaches and engages said switch operator and said electroresponsive means remains energized, further predetermined rotation of said disk and cam means causing said cam means to engage said switch for deenergizing said electroresponsive means to allow said stop elements to advance for one of them to be butted by an abutment element for stopping rotation of said base.

6. The apparatus according to claim 5 including movably mounted bracket means supporting said stop elements and electroresponsive means, and
- means coupled to the bracket members for decelerating said base with a constant force when said stop elements are butted by said abutment elements.

* * * * *